United States Patent [19]

Badylak et al.

[11] Patent Number: 5,554,389
[45] Date of Patent: Sep. 10, 1996

[54] URINARY BLADDER SUBMUCOSA DERIVED TISSUE GRAFT

[75] Inventors: Stephen F. Badylak, W. Lafayette; Sherry L. Voytik, Lafayette; Andrew Brightman, W. Lafayette; Matt Waninger, Frankfort, all of Ind.

[73] Assignee: Purdue Research Foundation, West Lafayette, Ind.

[21] Appl. No.: 418,763

[22] Filed: Apr. 7, 1995

[51] Int. Cl.$^6$ ................................................. A61K 35/22
[52] U.S. Cl. ............................... 424/558; 424/572; 623/1; 623/11; 623/12; 623/13; 623/14; 623/16; 623/18; 623/19; 623/20; 623/21
[58] Field of Search ............................ 424/558, 572; 623/1, 11, 12, 13, 14, 16, 18, 19, 20, 21

[56] References Cited

U.S. PATENT DOCUMENTS

| | | | |
|---|---|---|---|
| 4,902,508 | 2/1990 | Badylak et al. | 424/551 |
| 4,956,178 | 9/1990 | Badylak et al. | 424/551 |
| 5,275,826 | 1/1994 | Badylak et al. | 424/551 |
| 5,281,422 | 1/1994 | Badylak et al. | 424/551 |
| 5,352,463 | 10/1994 | Badylak et al. | 424/551 |
| 5,372,821 | 12/1994 | Badylak et al. | 424/551 |

OTHER PUBLICATIONS

"Comparison of Bovine Collagen Xenografts to Autografts in the Rabbit", J. C. Tauro, et al., *Clinical Orthopaedics and Related Research*, No. 266, May, 1991, pp. 271–284.

"Development of a Reconstituted Collagen Tendon Prosthesis", Jack D. Goldstein, et al., *The Journal of Bone and Joint Surgery, Incorporated*, vol. 71–A, No. 8, Sep. 1989, pp. 1183–1191.

"Replacement of Dog's Aorta by Autologous Intestinal Muscle in the Infected Retroperitoneum", R. Broll, et al., *Eurp. Surg. Res.*, 18: 390–396 (1986).

"Aortic Replacement with Multi–Layer Submucosa Prostheses Made From Heterologous Small Intestine", G. Rotthoff, et al., presented at 8th Congress of the Intenational Society of Cardiovascular Surgery, Vienna, Sep. 7–9, 1967.

"Replacement of the Abdominal Aorta by an Ileum Muscle Tube in an Animal Experiment", J. Huth, et al., (translation), *Thoraxchir. Vask, Chir.*, 15(4): 401–407, Aug. 1967.

"Long Term Observations and Histological Studies on Vessel and Heart Wall Grafts From Small Intestine", R. Haring, et al., (translation) *Langenbecks Arch. Klin. Chir.*, 1965, 313–664–8.

Primary Examiner—John W. Rollins
Assistant Examiner—Jean C. Witz
Attorney, Agent, or Firm—Barnes & Thornburg

[57] ABSTRACT

A tissue graft composition comprising bladder submucosal tissue delaminated from abluminal muscle layers and at least the luminal portion of the tunica mucosa of a segment of vertebrate urinary bladder is described. The graft composition can be implanted to replace or support damaged or diseased tissues.

10 Claims, No Drawings

URINARY BLADDER SUBMUCOSA DERIVED TISSUE GRAFT

FIELD OF THE INVENTION

The present invention relates to a tissue graft composition and methods for its preparation and use. More particularly, the present invention is directed to non-immunogenic tissue graft compositions comprising urinary bladder submucosa and use of same to promote endogenous tissue growth.

BACKGROUND AND SUMMARY OF THE INVENTION

It is known that compositions comprising the tunica submucosa of the intestine of warm-blooded vertebrates can be used advantageously as tissue graft materials. See U.S. Pat. Nos. 4,902,508 and 5,281,422. The tissue graft compositions described in those patents are characterized by excellent mechanical properties, including high compliance, a high burst pressure point, and an effective porosity index which allows such compositions to be used beneficially for vascular graft and connective tissue graft constructs. When used in such applications the graft constructs appear not only to serve as a matrix for the regrowth of the tissues replaced by the graft constructs, but, indeed, to promote or induce such regrowth of endogenous tissue. Common events to this remodeling process include: widespread and very rapid neovascularization, proliferation of granulation mesenchymal cells, biodegradation/resorption of implanted intestinal submucosal tissue material, and lack of immune rejection.

It is also known that intestinal submucosa can be fluidized by comminuting and/or protease digestion, without loss of its apparent biotropic properties, for use in less invasive methods of administration (e.g., by injection or topical application) to host tissues in need of repair. See U.S. Pat. No. 5,275,826.

There has been much additional research effort directed to finding other natural and synthetic materials having the requisite properties for use as tissue grafts. Surprisingly, it has been found that urinary bladder submucosa (UBS) prepared by delamination of bladder tissue of warm-blooded vertebrates exhibits mechanical and biotropic properties similar to that which has been reported for intestinal submucosal tissue. It can be substituted for intestinal submucosa tissue in most, if not all, of the applications previously reported for intestinal submucosa.

The tissue graft composition of the present invention comprises urinary bladder submucosa derived from urinary bladder tissue of a warm-blooded vertebrate. The wall of the urinary bladder is composed of the following layers: the tunica mucosa (including a transitional epithelium layer and the tunica propria), a submucosa layer, up to three layers of muscle and the adventitia (a loose connective tissue layer)—listed in thickness crossection from luminal to abluminal sides. Urinary bladder submucosa for use in accordance with the present invention is delaminated from the abluminal muscle layers and at least the luminal portion of the tunica mucosa of the urinary bladder tissue. The present graft composition can be implanted or injected into a vertebrate host to induce the repair or replacement of damaged or defective tissues.

DETAILED DESCRIPTION OF THE INVENTION

The tissue graft composition in accordance with the present invention comprises urinary bladder submucosa of a warm-blooded vertebrate delaminated from adjacent bladder tissue layers. The present tissue graft composition thus comprises the bladder submucosa delaminated from abluminal muscle cell layers and at least the luminal portion of the mucosal layer of a segment of urinary bladder of a warm-blooded vertebrate. Typically the delamination technique described below provides a tissue composition consisting essentially of urinary bladder submucosa. These compositions are referred to herein generically as urinary bladder submucosa (UBS).

UBS graft material is typically prepared from bladder tissue harvested from animals raised for meat production, including, for example, pigs, cattle and sheep or other warm-blooded vertebrates. Thus, there is an inexpensive commercial source of urinary bladder tissue for use in preparation of the tissue compositions in accordance with the present invention.

The preparation of UBS from a segment of urinary bladder is similar to the procedure for preparing intestinal submucosa detailed in U.S. Pat. No. 4,902,508, the disclosure of which is expressly incorporated herein by reference. A segment of urinary bladder tissue is first subjected to abrasion using a longitudinal wiping motion to remove both the outer layers (particularly the abluminal smooth muscle layers) and the luminal portions of the tunica mucosa layers—the epithelial layers). The resulting submucosa tissue has a thickness of about 80 micrometers, and consists primarily (greater than 98%) of a cellular, eosinophilic staining (H&E stain) extracellular matrix material. Occasional blood vessels and spindle cells consistent with fibrocytes are scattered randomly throughout the tissue. Typically the UBS is rinsed with saline and optionally stored in a frozen hydrated state until used as described below.

Fluidized UBS can be prepared in a manner similar to the preparation of fluidized intestinal submucosa, as described in U.S. Pat. No. 5,275,826 the disclosure of which is expressly incorporated herein by reference. The UBS is comminuted by tearing, cutting, grinding, shearing and the like. Grinding the UBS in a frozen or freeze-dried state is preferred although good results can be obtained as well by subjecting a suspension of submucosa pieces to treatment in a high speed (high shear) blender and dewatering, if necessary, by centrifuging and decanting excess water. Additionally, the comminuted fluidized tissue can be solubilized by enzymatic digestion of the bladder submucosa with a protease, such as trypsin or pepsin, or other appropriate enzymes for a period of time sufficient to solubilize said tissue and form a substantially homogeneous solution.

The present invention also contemplates the use of powder forms of UBS. In one embodiment a powder form of UBS is prepared by pulverizing urinary bladder submucosa tissue under liquid nitrogen to produce particles ranging in size from 0.1 to 1mm$^2$. The particulate composition is then lyophilized overnight and sterilized to form a solid substantially anhydrous particulate composite. Alternatively, a powder form of UBS can be formed from fluidized UBS by drying the suspensions or solutions of comminuted UBS.

The UBS tissue compositions of the present invention lend themselves to a wide variety of surgical applications relating to the repair or replacement of damaged tissues, including, for example the repair of vascular and connective tissues. Connective tissues for the purposes of the present invention includes bone, cartilage, muscle, tendons, ligaments, and fibrous tissue including the dermal layer of skin.

In accordance with the present invention, the graft compositions of the present invention are used advantageously to induce the formation of endogenous tissue at a desired site in a warm blooded vertebrate. Compositions comprising urinary bladder submucosa can be administered to a vertebrate host in an amount effective to induce endogenous tissue growth at a site in the host in need of same due to the presence of damaged or diseased tissue. The UBS compositions can be administered to the host in either solid or sheet form, by surgical implantation, or in fluidized form, by injection.

In one embodiment the present UBS compositions in sheet form can be used to form vascular grafts. The diameter of the graft should be about the same as the diameter of the recipient blood vessel. This is accomplished by manipulating the UBS to define a cylinder having diameter approximately the same as that of the recipient blood vessel and suturing or otherwise securing the tissue graft longitudinally to form said vascular graft. Thus, for example, a vascular graft can be prepared by selecting a sterile glass rod having an outer diameter equal to that of the recipient blood vessel, wrapping the UBS sheet around the glass rod and gathering the redundant tissue. The desired lumen diameter is achieved by suturing along the length of the graft (for example, using two continuous suture lines or a simple interrupted suture line) or by using other art-recognized tissue securing techniques. The vascular graft is surgically substituted for a damaged or diseased blood vessel using standard vascular surgery techniques.

Consistent with the use of UBS as a vascular graft material, UBS possesses mechanical properties highly desirable for such tissue graft materials, including low porosity index, high compliance, and a high burst pressure point. Those skilled in the art will appreciate that vascular graft material must be of low enough porosity to prevent intraoperative hemorrhage and yet of high enough porosity to allow extension of a newly-developed vasa vasorum through the graft material to nourish the luminal surface. Porosity of a graft material is typically measured in terms of ml of water passed per $cm^2 min^{-1}$ at a pressure of 120 mm Hg. UBS has a differential porosity to deionized water at 120 mm Hg pressure. The "porosity index" for UBS from the luminal toward abluminal direction is approximately 6.0; whereas the porosity index in the opposite direction is approximately 50. This property of differential porosity has also been noted for intestinal submucosal tissue but the values are an order of magnitude less than those values for UBS.

The UBS segments can also be used in accordance with this invention as a tissue graft construct for use in the repair or replacement of connective tissues using the same procedures described for use of intestinal submucosa in U.S. Pat. No. 5,281,422 and 5,352,463, expressly incorporated herein by reference. The UBS composition can be used in its delaminated natural sheet form or it can be cut longitudinally or laterally to form elongated tissue segments. Such segments or sheets have an intermediate portion, and opposite end portions and opposite lateral portions which can be formed for surgical attachment to existing physiological structures, using surgically acceptable techniques.

The grafts formed and used in accordance with this invention, upon implantation, undergo biological remodelling. They serve as a rapidly vascularized matrix for support and growth of new endogenous connective tissue. When used as a tissue graft material UBS has been found to be trophic for host tissues with which it is attached or otherwise associated in its implanted environment. The graft material has been found to be remodelled (resorbed and replaced with autogenous differentiated tissue) to assume the characterizing features of the tissue(s) with which it is associated at the site of implantation. In tendon and ligament replacement studies the graft appears to develop a surface that is synovialized. Additionally, the boundaries between the graft and endogenous tissue are no longer discernible. Indeed, where a single graft "sees" multiple microenvironments as implanted, it is differentially remodeled along its length. Thus, for example, when used in cruciate ligament replacement experiments, not only does the portion of the graft traversing the joint become vascularized and actually grow to look and function like the original ligament, but the portion of the graft in the femoral and tibial bone tunnels rapidly incorporates into and promotes development of the cortical and cancellous bone in those tunnels.

For tendon and ligament replacement applications, and other connective tissue repair applications UBS graft constructs are typically preconditioned by stretching longitudinally to a length longer than the length of the urinary bladder submucosa from which the graft construct was formed. One method of "pre-conditioning" involves application of a given load to the urinary bladder submucosa for three to five cycles. Each cycle consists of applying a load to the graft material for five seconds, followed by a ten second relaxation phase. Three to five cycles produces a stretch-conditioned graft material with reduced strain. The graft material does not return to its original size; it remains in a "stretched" dimension. For example, a UBS segment can be conditioned by suspending a weight from said segment, for a period of time sufficient to allow about 10 to about 20% or more elongation of the tissue segment. Optionally, the graft material can be preconditioned by stretching in the lateral dimension. The graft material exhibits similar viscoelastic properties in the longitudinal and lateral dimensions.

The graft segment is then formed in a variety of shapes and configurations, for example, to serve as a ligament or tendon replacement or a patch for a broken or severed tendon or ligament. Preferably, the segment is shaped and formed to have a layered or even a multilayered configuration with at least the opposite end portions and/or opposite lateral portions being formed to have multiple layers of the graft material to provide reinforcement for attachment to physiological structures, including bone, tendon, ligament, cartilage and muscle. In a ligament replacement application, opposite ends are attached using standard surgical technique to first and second bones, respectively, the bones typically being articulated as in the case of a knee joint.

The end portions of the UBS material can be formed, manipulated or shaped to be attached, for example, to a bone structure in a manner that will reduce the possibility of graft tearing at the point of attachment. Preferably the material can be folded or partially exerted to provide multiple layers for gripping, for example, with spiked washers or staples.

Alternatively, the UBS material may be folded back on itself to join the end portions to provide a first connective portion to be attached, for example, to a first bone and a bend in the intermediate portion to provide a second connective portion to be attached to a second bone articulated with respect to the first bone. For example, one of the end portions may be adapted to be pulled through a tunnel in, for example, the femur and attached thereto, while the other of the end portions may be adapted to be pulled through a tunnel in the tibia and attached thereto to provide a substitute for the natural cruciate ligament, the segment being adapted to be placed under tension between the tunnels to provide a ligament function, i.e., a tensioning and positioning function provided by a normal ligament.

The present UBS composition may be sterilized using conventional sterilization techniques including tanning with glutaraldehyde, formaldehyde tanning at acidic pH, ethylene oxide treatment, propylene oxide treatment, gas plasma sterilization, gamma radiation, and peracetic acid sterilization. A sterilization technique which does not significantly weaken the mechanical strength and biotropic properties of the graft is preferably used. For instance, it is believed that strong gamma radiation may cause loss of strength in the graft material. Because one of the most attractive features of these intestinal submucosa grafts is their ability to induce host-remodelling responses, it is desirable not to use a sterilization approach which will detract from that property. Preferred sterilization techniques include exposing the graft to peracetic acid, low dose gamma irradiation and gas plasma sterilization; peracetic acid sterilization being the most preferred method. Typically, after the tissue graft composition has been sterilized, the composition is wrapped in a porous plastic wrap and sterilized again using electron beam or gamma irradiation sterilization techniques.

We claim:

1. A composition comprising urinary bladder submucosa delaminated from both the abluminal muscle layers and at least the luminal portion of the tunica mucosa of a segment of a urinary bladder of a warm blooded vertebrate.

2. The composition of claim 1 wherein the urinary bladder submucosa is fluidized.

3. The composition of claim 1 wherein the urinary bladder submucosa is digested with a protease for a period of time sufficient to solubilize the tissue and provide a substantially homogenous solution.

4. The composition of claim 1, wherein the urinary bladder submucosa is dried and in powder form.

5. The composition of claim 1 formed into a cylinder having a predetermined luminal diameter and sutured along the length of the cylinder.

6. The composition of claim 1 conditioned for use as a connective tissue substitute by stretching to produce a graft construct longer than the segment of urinary bladder tissue from which it is formed.

7. A non-immunogenic tissue graft composition capable of inducing endogenous connective tissue growth when implanted in warm-blooded vertebrates, said composition comprising urinary bladder submucosa delaminated from both the abluminal muscle layers and at least the luminal portion of the tunica mucosa of a segment of a urinary bladder of a warm-blooded vertebrate.

8. A method for inducing the formation of endogenous connective tissue at a site in need of endogenous tissue growth in a warm blooded vertebrate, said method comprising transplanting a graft composition comprising urinary bladder submucosa in an amount effective to induce endogenous connective tissue growth at the site the composition is administered.

9. The method of claim 8, wherein the graft composition is fluidized and is administered by injection into the warm-blooded vertebrate.

10. The method of claim 8, wherein the graft composition is administered by surgically implanting the composition into the warm-blooded vertebrate.

\* \* \* \* \*